United States Patent
Matsumoto

(10) Patent No.: US 7,782,507 B2
(45) Date of Patent: Aug. 24, 2010

(54) IMAGE PROCESSING METHOD AND COMPUTER READABLE MEDIUM FOR IMAGE PROCESSING

(75) Inventor: Kazuhiko Matsumoto, Tokyo (JP)

(73) Assignee: Ziosoft, Inc., Tokyo (JP)

( * ) Notice: Subject to any disclaimer, the term of this patent is extended or adjusted under 35 U.S.C. 154(b) by 904 days.

(21) Appl. No.: 11/619,300

(22) Filed: Jan. 3, 2007

(65) Prior Publication Data
US 2007/0154075 A1 Jul. 5, 2007

(30) Foreign Application Priority Data
Jan. 5, 2006 (JP) .............................. 2006-000763

(51) Int. Cl.
*G03F 3/10* (2006.01)
*H04N 1/46* (2006.01)
*G06K 9/00* (2006.01)
*G06K 9/20* (2006.01)

(52) U.S. Cl. ...................... 358/527; 358/537; 358/538; 358/1.9; 382/128; 382/282

(58) Field of Classification Search ................. 358/537, 358/538, 527, 1.9; 345/424, 422, 425; 382/128, 382/282, 224
See application file for complete search history.

(56) References Cited

U.S. PATENT DOCUMENTS
5,666,476 A    9/1997  Kawanaka
5,986,662 A *  11/1999  Argiro et al. ................. 345/424
2007/0276214 A1* 11/2007  Dachille et al. ............. 600/407

FOREIGN PATENT DOCUMENTS
JP   02-39382 A     2/1990
JP   04-295342 A   10/1992
JP   2001-092945 A  4/2001

OTHER PUBLICATIONS
Japanese Office Action issued Jun. 26, 2009.
Japanese Office Action, issued Dec. 19, 2008.

* cited by examiner

Primary Examiner—Charlotte M Baker
(74) Attorney, Agent, or Firm—Pearne & Gordon LLP

(57) ABSTRACT

A preview image is operated and an original image is opened based on the operation result of the preview image. For example, a heart is rotated from side to side on a preview screen, and the heart is displayed at a certain rotation angle and a certain magnifying scale power in the preview image. If the image is opened, the original image (heart) can be opened while maintaining the operated rotation angle and the magnifying scale power in the preview.

11 Claims, 13 Drawing Sheets

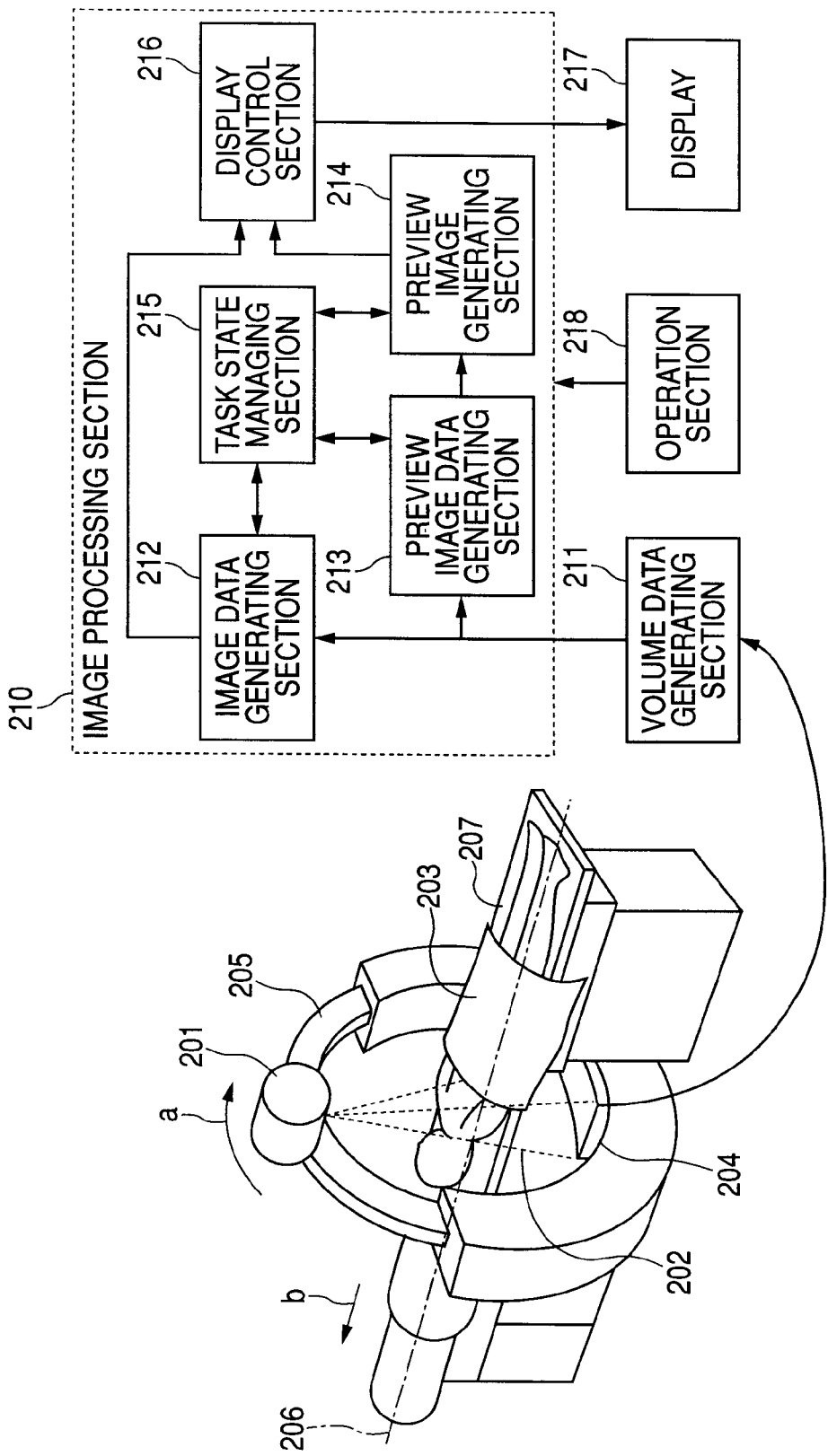

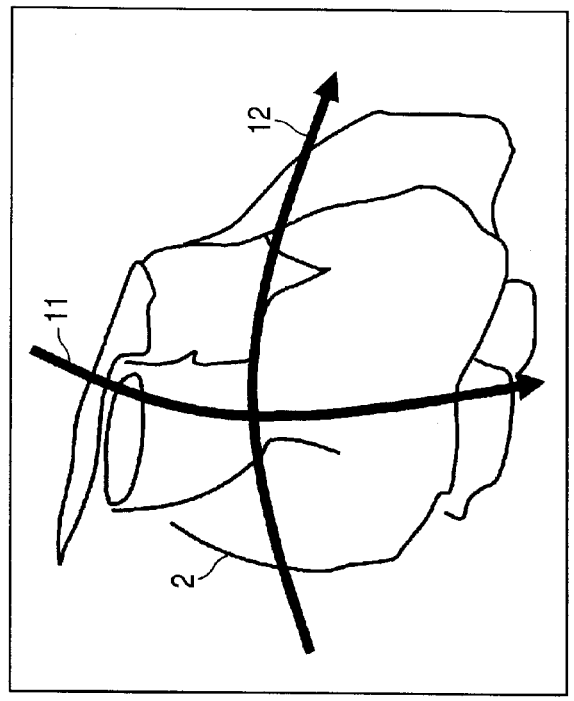

FIG. 5

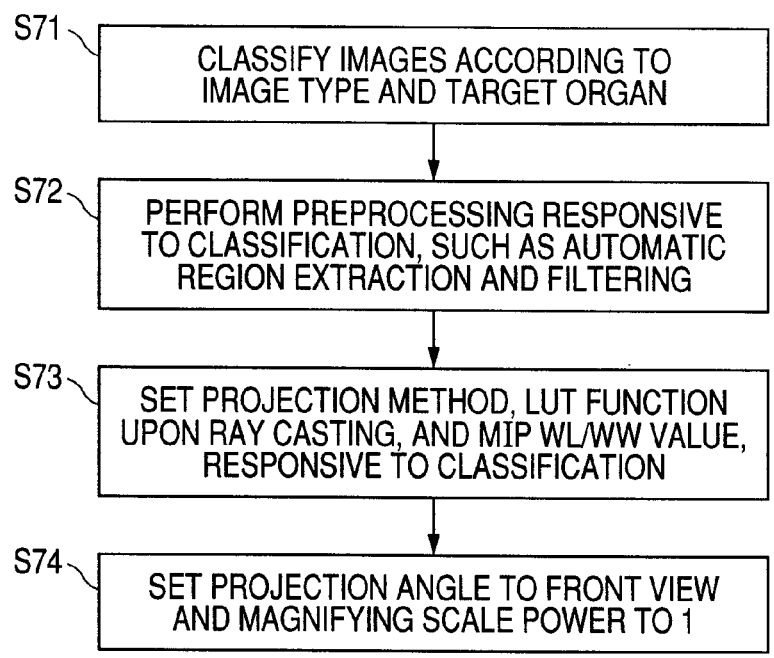

S71 — CLASSIFY IMAGES ACCORDING TO IMAGE TYPE AND TARGET ORGAN

S72 — PERFORM PREPROCESSING RESPONSIVE TO CLASSIFICATION, SUCH AS AUTOMATIC REGION EXTRACTION AND FILTERING

S73 — SET PROJECTION METHOD, LUT FUNCTION UPON RAY CASTING, AND MIP WL/WW VALUE, RESPONSIVE TO CLASSIFICATION

S74 — SET PROJECTION ANGLE TO FRONT VIEW AND MAGNIFYING SCALE POWER TO 1

FIG. 6

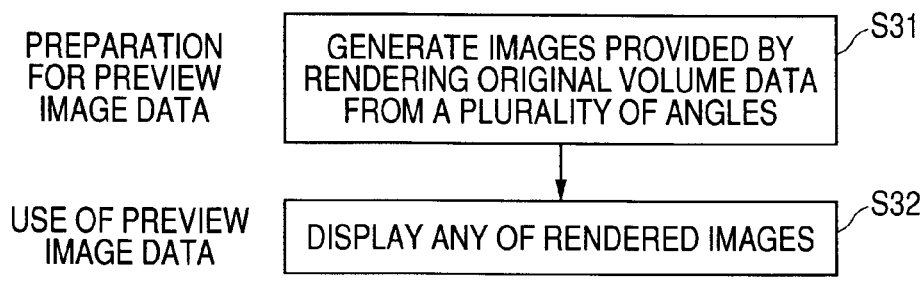

PREPARATION FOR PREVIEW IMAGE DATA — GENERATE IMAGES PROVIDED BY RENDERING ORIGINAL VOLUME DATA FROM A PLURALITY OF ANGLES — S31

USE OF PREVIEW IMAGE DATA — DISPLAY ANY OF RENDERED IMAGES — S32

| PATIENT A | 200X YEAR | Y MONTH | Z DAY | CT |
| PATIENT B | 200A YEAR | B MONTH | C DAY | CT |
| PATIENT C | 200X YEAR | G MONTH | J DAY | MRI |
| PATIENT D | 200A YEAR | F MONTH | K DAY | CT |
| PATIENT E | 200X YEAR | F MONTH | D DAY | PET-CT |

| HEART 1 | XX TIME | Y0 MINUTE | 256 SLICES |
| HEART 2 | XX TIME | Y1 MINUTE | 256 SLICES |
| HEART 3 | XX TIME | Y2 MINUTE | 128 SLICES |
| ENTIRE BODY | XX TIME | Y3 MINUTE | 1 SLICE |

IMAGE PROCESSING METHOD AND COMPUTER READABLE MEDIUM FOR IMAGE PROCESSING

This application claims foreign priority based on Japanese Patent application No. 2006-000763, filed Jan. 5, 2006, the content of which is incorporated herein by reference in its entirety.

BACKGROUND OF THE INVENTION

1. Field of the Invention

This invention relates to an image processing method and a computer readable medium for image processing, for displaying an image using volume data such as a medical image.

2. Description of the Related Art

In recent years, attention has been focused on a technology of visualizing inside of a three-dimensional object with the progression of the image processing technology using a computer. Particularly, medical diagnosis using a CT (Computed Tomography) apparatus or an MRI (Magnetic Resonance Imaging) apparatus capable of visualizing inside of a living body to find a lesion at an early stage is widely conducted in medical field.

A method called volume rendering is known as a method of providing a three-dimensional image of the inside of an object. In the volume rendering, a virtual ray is projected to a three-dimensional volume data filled with voxel (minute volume element), whereby an image is projected onto a projection plane. A ray casting method is one kind of volume rendering. In the ray casting method, sampling is performed at given intervals along the ray path, the voxel value is acquired from the voxel at each sampling point, and color information and opacity are calculated from the voxel values.

Voxel is a unit of a three-dimensional region of an object, and the voxel value is unique data representing the characteristic of the density value, etc., of the voxel. The whole object is represented by voxel data, which is typically a three-dimensional array of the voxel values. Usually, two-dimensional tomographic image data provided by a CT apparatus are accumulated along the direction perpendicular to the tomographic plane, and necessary interpolation is performed, whereby voxel data of a three-dimensional array is provided.

Volume data and image data provided by processing the volume data are stored in a server or a client computer. The image stored in the computer is opened (namely, the image data stored in the computer is accessed), whereby the computer can read the image data and execute a predetermined image processing program for displaying the image in a user-operable state. Before the image is opened, a user can view a preview image of the image. In a certain system, as for an image not yet opened, a 2D (two-dimensional) slice image (cross-sectional image) is displayed as a preview image; as for an image once opened, an image in the last edit state (often, a 3D image: three-dimensional image) is displayed.

FIG. 13C shows a preview image when images of "patient D" and "heart 2" are selected out of menus shown in FIGS. 13A and 13B. This preview image is for an image once opened, and the image (heart 2) last displayed in a previous task by the user (in a last edit state) is displayed. The preview image is not made by rendering at that time. The preview image is only a copy of the image displayed on the screen as a result of the previous task and therefore its internal entity is a 2D image.

FIG. 14 shows an outline of a flow in a related art for opening an image. It is assumed that image data is stored in a server, etc., on a network. When the user completes an edit task of an image (S101), task state for the image is stored (step S102). When the task state is stored, the last image displayed on the monitor is stored (step S103). The task state and the last displayed image are transferred from the computer as the client to the server (step S108).

Next, the user selects an image (step S104). Then, the last displayed image (if the image is not yet opened, one slice image) is transferred from the server to the computer of the client (step S109). Accordingly, the last image displayed on the monitor (if the image is not yet opened, one slice image) is displayed as a preview image (step S105). When the user performs an operation to open the image with respect to the preview image (step S106), the task state and the image data are transferred from the server to the computer as the client (step S110). Accordingly, the image is opened using the stored task state (step S107). More than one task state may be generated for the same image data because a plurality of features involved in the same image data may be rendered under different conditions.

On the other hand, hitherto, fly through display has been used in performing virtual endoscope display. The fly through display is to display a moving image as if flying through a human body, by moving a view point along the previously generated path in performing virtual endoscope display.

FIG. 15 shows an example of the fly through display of a virtual endoscope image in a related art. FIG. 16 is a schematic representation of the fly through display in the related art. In an endoscopy in the related art, as shown in FIG. 16, projection is conducted from a view point 111 onto a projection plane 110 to generate an image as a display image 112 (step S201 in FIG. 15). In this case, the fly through display is a moving image and therefore a plurality of display images 112 is stored in time sequence (step S202). At the preview display time, the display images 112 are called and are displayed as a moving image (step S203).

Thus, for the preview image in the related art, if the image is an image opened in the previous task, only one image in the last edit state displayed on the screen is displayed. On the other hand, if the image is an image not yet opened, namely, an image whose image data is not read and for which a predetermined image processing program is not yet executed, only one 2D slice (cross-sectional image) is displayed.

Therefore, if a plurality of images of the same patient exists, if more than one task state exists for the same image, etc., the preview images resemble and if the preview images are provided at different angles, it becomes more difficult to distinguish the preview images from each other. Thus, it is hard to determine which image or which state related to the image is to be opened. Particularly, the size of the image data including volume data is large and it takes time from acceptance of an instruction to display the image until the image is displayed and therefore it may be difficult to open appropriate image data with good operability.

In the fly through display in the related art, when operating image data, the direction of the view point can be changed dynamically even while fly through display is produced as a moving image, and the region of interest can be displayed at an angle easy to be viewed.

However, when viewing the preview image of the fly through display in the related art, although a moving image with the view point moving on the path can be displayed, the view point is fixed to the direction specified at the moving image generation time. A field of view not included in the previously specified view point is not displayed as a preview, and therefore it may be difficult to select the objective image rapidly.

SUMMARY OF THE INVENTION

The present invention has been made in view of the above circumstances, and provides an image processing method and a computer readable medium for image processing capable of determining an objective image data and task properties rapidly and reliably by using a preview image, in which operation performed at the determination time on image data and task properties is inherited to make a smooth transition to a diagnosing task.

In some implementations, an image processing method of the invention comprising:

generating a preview image by using preview image data that are prepared based on volume data;

displaying the generated preview image;

accepting operation on the displayed preview image; and displaying an original image corresponding to the preview image in response to an instruction to display the original image, wherein the operation on the preview image is reflected in the original image.

According to the described configuration, the preview image can be operated and thus if a plurality of similar medical images exist, the objective image can be reliably determined by changing the display angle, the magnifying scale factor, etc., of the preview image. According to the described configuration, to display the objective medical image, the medical image in which operation for the preview image is reflected is displayed, whereby operation for the medical image can be performed following the operation performed for the preview image, so that the user can conduct smooth diagnosis, etc., using the medical image.

In the image processing method, the preview image data include surface data that are prepared based on the volume data. In the image processing method, the preview image data include a plurality of two-dimensional images that is prepared based on the volume data.

According to the described configuration, the preview image data is data that does not require volume rendering, so that the size of the preview image data can be lessened and the preview image processing load can be lightened and the preview image can be displayed with good operability.

In the image processing method, the preview image data are automatically prepared. In the image processing method, the preview image data are prepared by using completion of a task by a user as a trigger. In the image processing method, the preview image data are prepared by using storing of the volume data as a trigger.

According to the described configuration, the preview image data is previously prepared, whereby when the preview image is operated, the preview image in which the previous operation is reflected can be displayed rapidly.

In the image processing method, initial values of a task state for the preview image are generated by using acquisition of the volume data as a trigger, and the preview image is generated by using the preview image data and the initial values of the task state.

According to the described configuration, even a preview image not yet displayed (where no task occurs) can be displayed so as to be viewed easily.

In the image processing method, the prepared preview image data are stored in a server. In the image processing method, the prepared preview image data are stored in a client.

According to the described configuration, the preview image data can be stored separately in the server or the client. Thus, for example, a specialist in image processing may perform the preparation stage for the preview image data such as image extraction and coloring, and a doctor may immediately use the preview image processed so as to be viewed easily at the same terminal or a different terminal. Thus, operation at each stage can be performed smoothly.

In the image processing method of the invention, the preview image is an image representing a task result by the user. The image processing method further comprising: displaying an image being generated as a result of a task by a user.

According to the described configuration, not only the preview image, but also the image generated as a result of the task of the user is displayed. Thus, if the preview image is inferior in point of quality to the original medical image, the objective image can be determined rapidly from among a large number of images with reference to the good-quality medical image. Particularly, it is effective to first display the high-quality image generated as a result of the task, and after the user performs an operation onto the image, display a preview image responsive to the operation.

In some implementations, a computer readable medium of the invention having a program including instructions for permitting a computer to perform image processing, the instructions comprising:

generating a preview image by using preview image data that are prepared based on volume data;

displaying the generated preview image;

accepting operation on the displayed preview image; and displaying an original image corresponding to the preview image in response to an instruction to display the original image, wherein the operation on the preview image is reflected in the original image.

According to the image processing method and the computer readable medium for image processing of the invention, the operation performed when the preview image of image data is operated to determine is inherited when the image data is opened, whereby the original image in which the operation is reflected is displayed, so that the image can be operated following the operation performed for the preview image and thus the user can conduct smooth diagnosis, etc., using the original image.

BRIEF DESCRIPTION OF THE DRAWINGS

In the accompanying drawings:

FIG. 1 is a drawing to schematically show a computed tomography (CT) apparatus used with an image processing method according to one embodiment of the invention;

FIGS. 2A and 2B are menus to select patient and object in the image processing method according to one embodiment of the invention;

FIG. 2C is a drawing to show a preview image when "patient D" and "heart 2" are selected out of menus shown in FIGS. 2A and 2B in the image processing method according to one embodiment of the invention;

FIG. 5 is a flowchart to show a method of setting the initial values of the task state in one embodiment of the invention;

FIG. 6 is a flowchart to show a preview image generating method 1 (storing of a plurality of rendering results) in the image processing method of one embodiment of the invention;

DESCRIPTION OF THE PREFERRED EMBODIMENTS

Figure 3C:
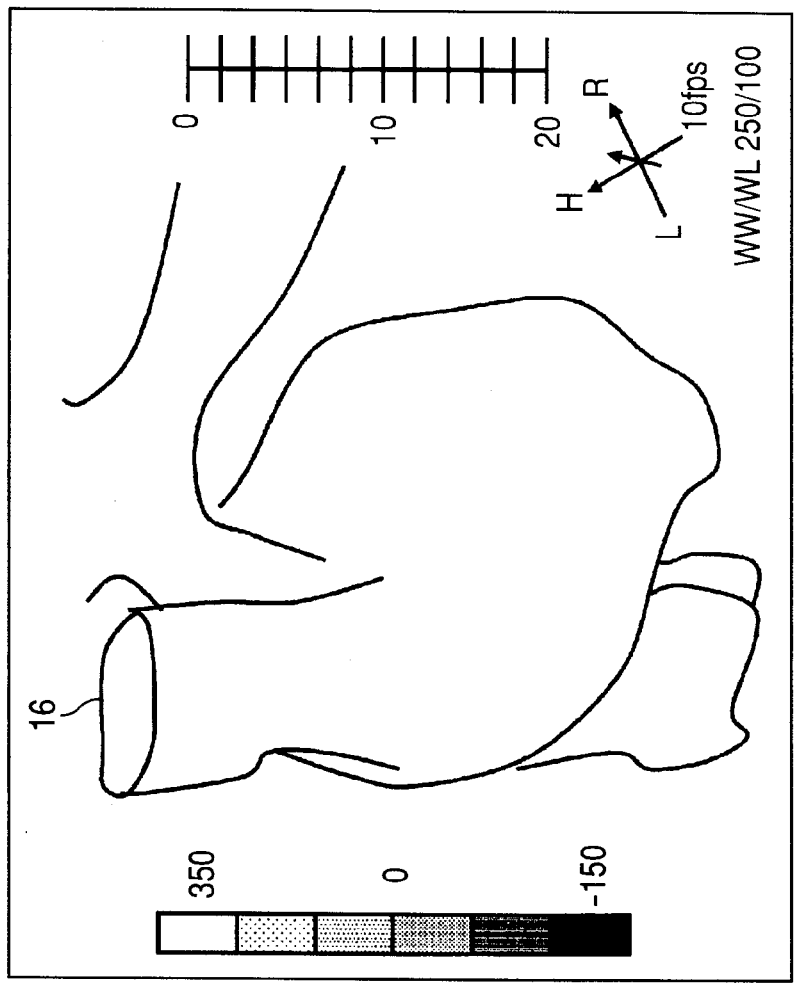
FIGS. 3A-3C are schematic representations for operating a preview image and opening the original image based on the operation result in the image processing method according to one embodiment of the invention.

FIG. 1 schematically shows a computed tomography (CT) apparatus used in an image processing method according to an embodiment of the invention. The computed tomography apparatus is used for visualizing tissues, etc., of a subject. A pyramid-like X-ray beam 202 having edge beams which is represented by dotted lines in FIG. 1 is emitted from an X-ray source 201. The X-ray beam 202 is applied on an X-ray detector 204 after transmitting through the subject, for example, a patient 203. In this embodiment, the X-ray source 201 and the X-ray detector 204 are disposed in a ring-like gantry 205 so as to face each other. The ring-like gantry 205 is supported by a retainer not shown in FIG. 1 so as to be rotatable (see the arrow "a") about a system axis 206 which passes through the center point of the gantry.

The patient 203 is lying on a table 207 through which the X-rays are transmitted. The table 207 is supported by a retainer which is not shown in FIG. 1 so as to be movable (see the arrow "b") along the system axis 206.

Thus a CT system is configured so that the X-ray source 201 and the X-ray detector 204 are rotatable about the system axis 206 and movable along the system axis 206 relatively to the patient 203. Accordingly, X-rays can be cast on the patient 203 at various projection angles and in various positions with respect to the system axis 206. An output signal from the X-ray detector 204 when the X-rays are cast on the patient 203 are supplied to a volume data generating section 211 and converted into a volume data.

In sequence scanning, the patient 203 is scanned in accordance with each sectional layer of the patient 203. When the patient 203 is scanned, while the X-ray source 201 and the X-ray detector 204 rotate around the patient 203 about the system axis 206 as its center, the CT system including the X-ray source 201 and the X-ray detector 204 captures a large number of projections to scan each two-dimensional sectional layer of the patient 203. A tomogram displaying the scanned sectional layer is reconstructed from the measured values acquired at that time. While the sectional layers are scanned continuously, the patient 203 is moved along the system axis 206 every time the scanning of one sectional layer is completed. This process is repeated until all sectional layers of interest are captured.

On the other hand, during spiral scanning, the table 207 moves along the direction of the arrow "b" continuously while the CT system including the X-ray source 201 and the X-ray detector 204 rotates about the system axis 206. That is, the CT system including the X-ray source 201 and the X-ray detector 204 moves on a spiral track continuously and relatively to the patient 203 until the region of interest of the patient 203 is captured completely. In this embodiment, signals of a large number of successive sectional layers in a diagnosing area of the patient 203 are supplied to a volume data generating section 211 by the computed tomography apparatus shown in FIG. 1.

Volume data generated by the volume data generating section 211 is introduced into an image data generating section 212 and a preview image data generating section 213 in an image processing section 210. The image data generating section 212 refers to a task state managed by a task state managing section 215 (described later) and generates original image using the volume data generated by the volume data generating section 211. The preview image data generating section 213 generates preview image data which is data used to generate a preview image corresponding to the image data based on the volume data generated by the volume data generating section 211 and the task state managed by the task state managing section 215. A preview image generating section 214 refers to the task state managed by the task state managing section 215 and generates a preview image using the preview image data generated by the preview image data generating section 213. The task state managing section 215 manages parameters of angle, magnifying scale factor, pan, WL/WW (windowlevel), etc., as the task state. The task state is information provided as a result of user operation and is separate from the preview image data. Upon reception of a command for changing the display angle, etc., for the preview image displayed on a display 217 from an operation section 218, the task state managing section 215 updates the task state to the content responsive to the command and stores the updated task state. A display control section 216 displays the original image, the preview image, etc., generated by the image data generating section 212 and the preview image generating section 214 on the display 217. The display 217 produces display of original image as well as animation display to display a plurality of images in sequence, etc., display of a plurality of preview images, and parallel display of preview image and original image, under the control of the display control section 216.

The operation section 218 sets the display angle for the preview image, specifies the magnifying scale power, etc., in response to an operation signal from a keyboard, a mouse, etc. The operation section 218 generates a control signal of each setup value and supplies the control signal to each functional block. Accordingly, while seeing the preview image displayed on the display 217, the user can change the preview image interactively and can select the volume data through checking the preview image data. The preview image data generating section 213 is not an indispensable component and the preview image generating section 214 may generate a preview image using preview image data previously generated in an external system.

FIG. 2C shows a preview image when images of "patient D" and "heart 2" are selected out of menus shown in FIGS. 2A and 2B. In the embodiment, simple operations can be performed on the preview image. For example, the preview image corresponding to "heart 2" in the menu (heart 2 in FIG. 2C) can be rotated vertically or from side to side as indicated by arrow 11 or 12. In this case, the parameters that can be operated are angle, magnifying scale factor, pan, WL/WW (window level), etc., for example.

In the image processing method according to the embodiment of the invention, the result of the operation performed on the preview image is reflected in the original image corresponding to the preview image, so that the user can easily check the image to be opened. Further, the parameters such as the display angle, etc., specified in the preview image can be inherited to the original image through the task state managing section 215 shown in FIG. 1, enabling the user to conduct smooth medical diagnosis using the image.

In this case, the preview image operation program and the predetermined image processing program may be a separate (another) program from or may be the same program. For example, to generate a preview data which are images provided by rendering original volume data from different angles (example 1 described later), a separate program is applied; to generate a preview data which is a volume data with a side size being a quarter the original volume data for preview (example 2 described later), the same program is used.

However, the preview image operation program and the image processing program applied to the original image differ in the data to be read. The preview image operation program reads the preview image data described later and the image processing program reads the volume data.

Figure 3A:
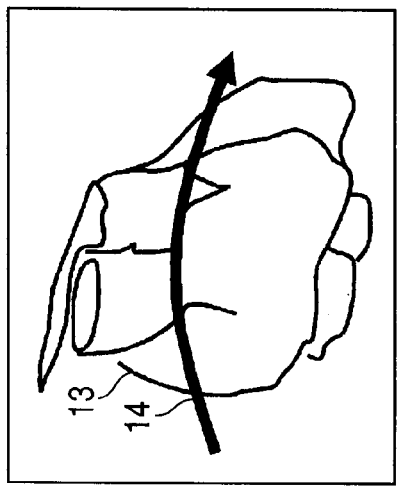
Figure 3B:
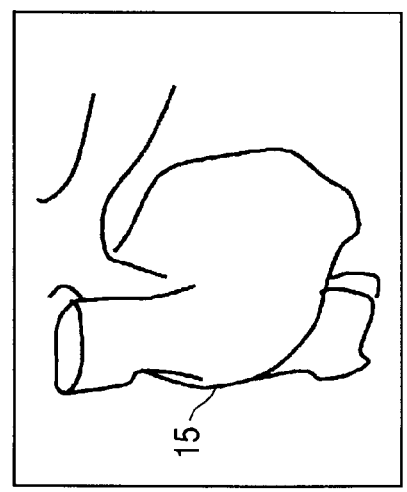

FIGS. 3A-3C show how a preview image is operated when the original image is opened based on the operation result in the image processing method according to the embodiment of the invention. That is, FIG. 3A and FIG. 3B show a preview image and FIG. 3C shows the original image after the volume data corresponding to the preview image is opened. A heart 13 is rotated from side to side on a preview screen as indicated by an arrow 14 and a heart 15 is displayed at any desired rotation angle and any desired magnifying scale power as shown in FIG. 3B. As the user performs an operation to open the original image of the volume data corresponding to the preview image, the original image (heart 16) is opened while the rotation angle and the magnifying scale power (here, the magnifying scale power is relative to the image size) applied to the preview image shown in FIG. 3B are maintained, as shown in FIG. 3C.

Thus, the operation result of the preview image is reflected in the image processing program to be executed after the original image is opened, so that the user can select the image to be opened rapidly from among a large number of image data (volume data). In addition, for displaying the preview image in any desired display state and can also continue medical diagnosis based on the original image without a sense of incompatibility. As a result of operating the preview image, the preview image is in a display state suited for being distinguished from other image data (volume data) and it can be expected that the display state of preview image will also be a display state suited for observing the original image.

Figure 4:
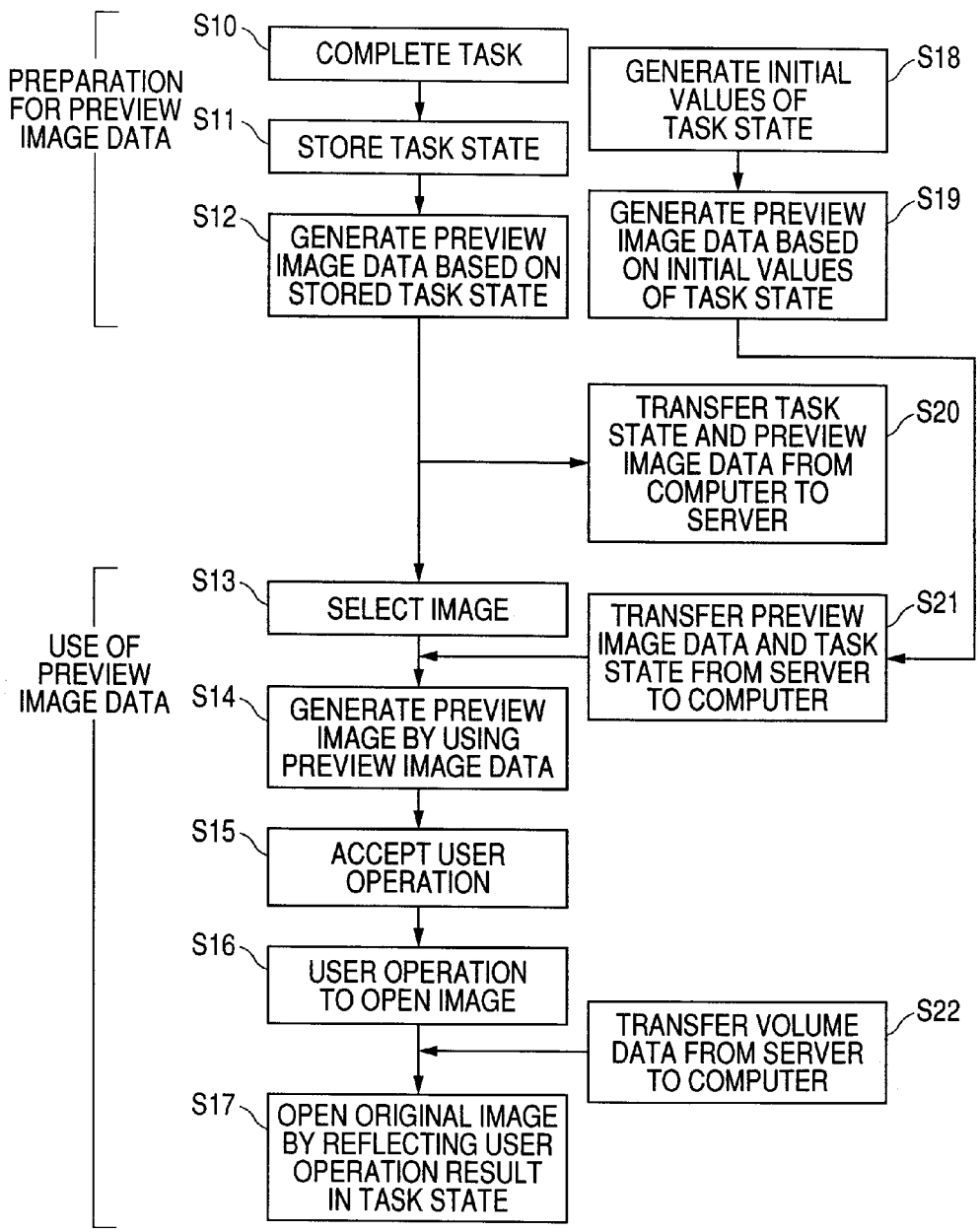
FIG. 4 is a flowchart of the image processing method of one embodiment of the invention.

FIG. 4 shows an outline of a flow of the image processing method of the embodiment of the invention. It is assumed that volume data is stored in a server, etc., on a network. In the image processing method of the embodiment, when the user completes an edit task of an original image (S10) at a preparation stage for preview image data, a task state for the original image (parameters of angle, magnifying scale factor, pan, WL/WW, etc., for example,) is stored (step S11). Preview image data is generated based on the stored task state of the original image (step S12). The task state and the preview image data are transferred from the computer of the client to the server (step S20).

On the other hand, if the volume data is not yet opened, initial values of the task state (parameters of angle, magnifying scale factor, pan, WL/WW, etc., for example,) are generated (step S18), and preview image data is generated according to the initialized task state (step 19). Thus a preview image can be displayed in the same manner as when the original image is already subjected to an edit task, enabling the user to easily recognize the objective image.

Next, when the user selects image data or the stored task state (step S13) at a use stage of the preview image data, the preview image data and the task state are transferred from the server to the computer of the client (step S21), and a preview image is generated using the preview image data and the task state (step S14). Then, an operation by the user on the preview image is accepted (step S15). When the user performs an operation to open the image (step S16), the volume data is transferred from the server to the computer of the client (step S22). Accordingly, the original image created from the volume data is opened with the result of the operation by the user being reflected in the stored task state of the original image.

In the embodiment, the operation flow is separated into the preparation stage for preview image data and the use stage of the preview image data, so that the preparation stage for preview image data can be automatically processed in the server, etc., and the use stage of the preview image data can be processed in the client which is actually operating the preview image. Accordingly, a radiologist may perform a manipulation of original image such as segmentation and coloring of the image, and a doctor can immediately use a preview image processed in an easy-to-see manner. This is effective particularly for the case where there are two or more operators. On the other hand, the embodiment can also be carried out in a stand-alone system by making the whole processing to be performed in the client computer.

FIG. 5 is a flowchart to show a method of setting the initial values of the task state to display a preview image for an original image not yet subjected to an edit task, in the same manner as a preview image for an original image already subjected to an edit task at S18 so that a user can easily recognize the objective image.

In the embodiment, to set the initial values of the task state, first, images are classified according to an image type (CT, MRI, or the like; time-series image or single image; etc.) and a target organ (step S71). Next, preprocessing responsive to the classification is performed (step S72). The preprocessing is automatic region extraction (deletion of bone, search for diseased part, etc.), filtering (noise removal, enhancement of feature shape, etc.) or the like.

Next, a projection method (ray casting, or MIP (maximum intensity projection), etc., and parallel projection or perspective projection), an LUT (look-up table) function upon ray casting, WL/WW value of MIP, or the like, responsive to the classification are set (step S73). The projection angle is set to a front view and the magnifying scale power is set to 1 (step S74).

If initial values of a task state are thus preset, even a preview image for an original image not yet subjected to an edit task can be displayed in the same manner as a preview image for an original image already subjected to an edit task, enabling the user to find the objective image rapidly.

Example 1

FIG. 6 is a flowchart to show a preview image generating method 1 (storing of a plurality of rendering results) in the image processing method of the embodiment of the invention. In the generating method, images provided by rendering the original volume data from a plurality of angles are generated (step S31) at the preparation stage for preview image data. At the use stage of the preview image data, any of the rendered images is displayed in association with user operation (step S32).

Figure 7:
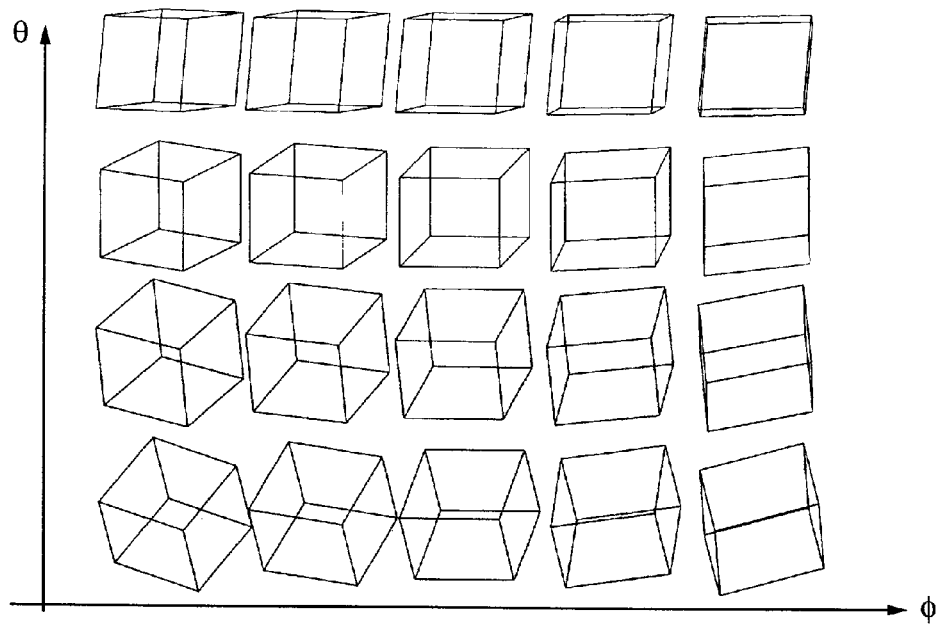
FIG. 7 is a schematic representation of the preview image generating method 1 (storing of a plurality of rendering results) in the image processing method of one embodiment of the invention.

FIG. 7 is a schematic representation of the preview image generating method 1 (storing of a plurality of rendering results) in the image processing method of the embodiment of the invention. In the generating method, images provided by rendering the original volume data from a plurality of angles are generated and are stored like a matrix in association with parameters θ and φ of an operation interface for preview images such as a mouse, etc., as shown in the figure. Any of the rendered images is displayed in response to the parameters θ and φ of a pointing device operated by the user. The image can also be scaled up or down.

Accordingly, the user can view the preview images in response to the desired angle, etc., and can rapidly find the objective image from among a large number of images. Since the original image can be opened according to the user-desired angle, etc., specified on the preview image, the user can continue medical diagnosis based on the original image without a sense of incompatibility.

Example 2

Figure 8:
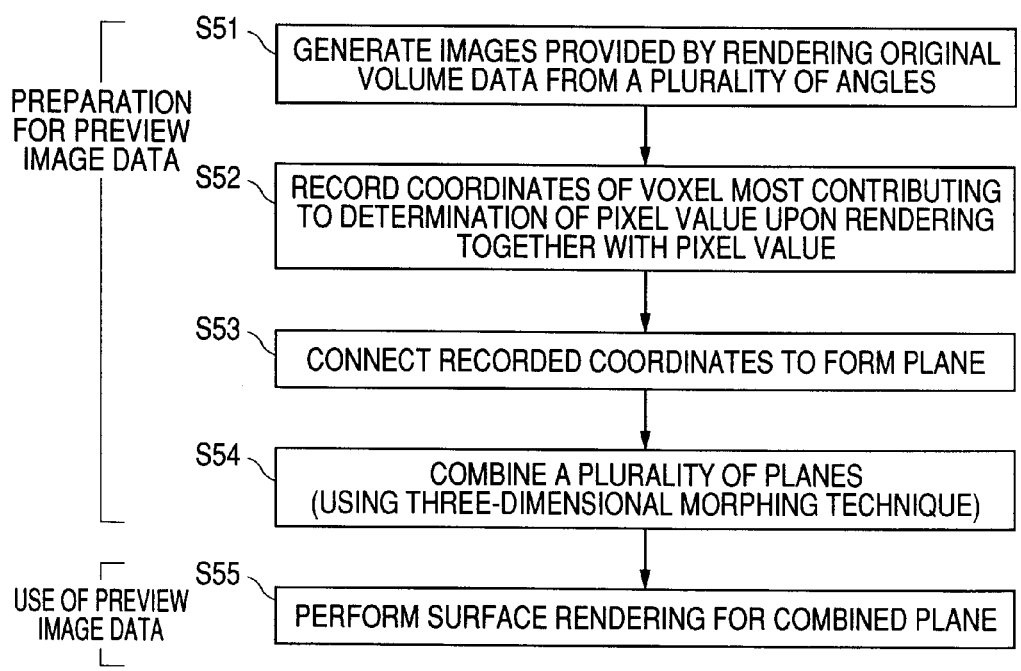
FIG. 8 is a flowchart to show a preview image generating method 2 (3D using surface rendering) in the image processing method of one embodiment of the invention.

FIG. 8 is a flowchart to show a preview image generating method 2 (3D by surface rendering) in the image processing method of the embodiment of the invention. In the generating method, images provided by rendering the original volume data from a plurality of angles are generated (step S51) at the preparation stage for preview image data.

Next, coordinates of the voxel most contributing to determination of a pixel value upon rendering are recorded together with the pixel value (step S52). The recorded coordinates are connected to form a plane and the pixel values are adopted as the pixel values of points on the plane upon rendering (step S53), and a plurality of planes is combined (using a three-dimensional morphing technique) (step S54). It is considered that the voxel most contributing to determination of the pixel value is the voxel most attenuating the virtual ray in the ray casting method, for example. It is considered that the voxel most contributing to determination of the pixel value is the voxel with the maximum value acquired on the virtual ray in the MIP method, for example.

Next, at the use stage of the preview image data, surface rendering is performed for the combined plane (step S55). In the embodiment, a preview image is generated using surface data as preview image data, so that the preview image can be simply displayed in response to the user-desired angle, etc. Since the original image can be opened while maintaining the angle, etc., specified for the preview image by the user, the user can continue medical diagnosis based on the original image without a sense of incompatibility.

Unlike in usual 3D volume rendering where volume data including data inside an object is retained, only the data of the surface of an object is retained in the surface rendering in the embodiment. Since the data size of the surface data is small as compared with that of the volume data, the preview image that can be operated can be generated easily and the processing load can be lightened in the embodiment.

Example 3

Figure 9A:
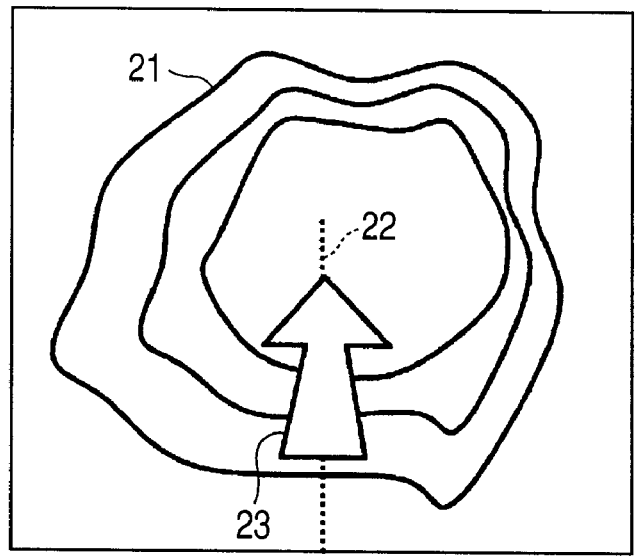
FIGS. 9A and 9B are schematic representations for producing fly through display of an endoscope image in a preview image of one embodiment of the invention.
Figure 9B:
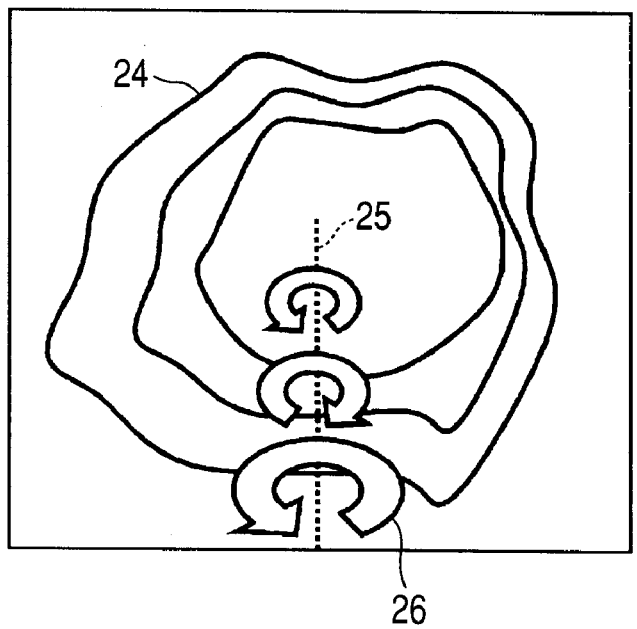

FIGS. 9A and 9B are schematic representations for producing fly through display of an endoscope image in a preview image of the embodiment of the invention. In the preview image in the related art, a moving image with a view point 23 moving on a path 22 in an intestine 21 can be displayed as shown in FIG. 9A, but the degree of freedom is only one dimension. Then, in the embodiment, a sight line direction 26 can also be rotated while the view point is moving on a path 25 in an intestine 24 in a preview image, as shown in FIG. 9B.

Figure 10:
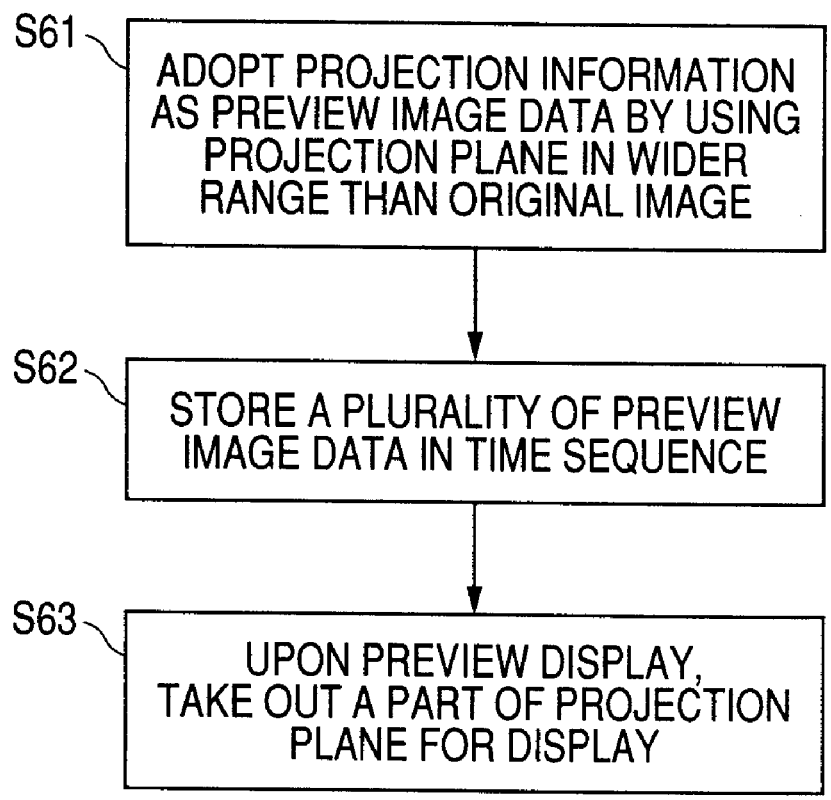
FIG. 10 is a flowchart for producing fly through display of an endoscope image in a preview image of one embodiment of the invention.
Figure 11A:
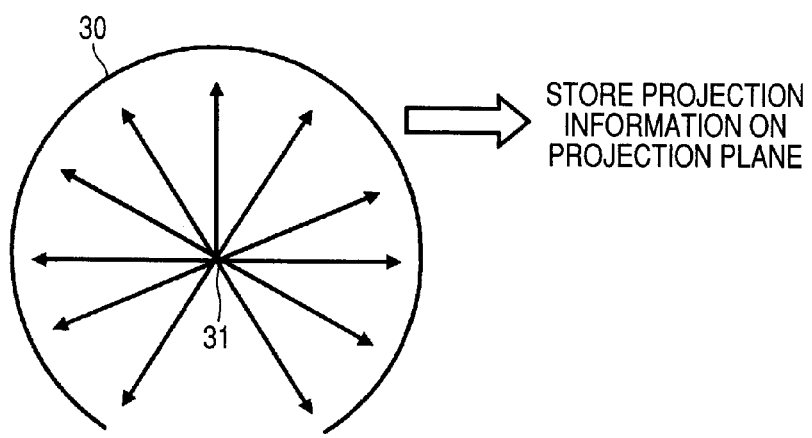
FIGS. 11A and 11B are schematic representations for producing fly through display of the endoscope image in the preview image of one embodiment of the invention.
Figure 11B:
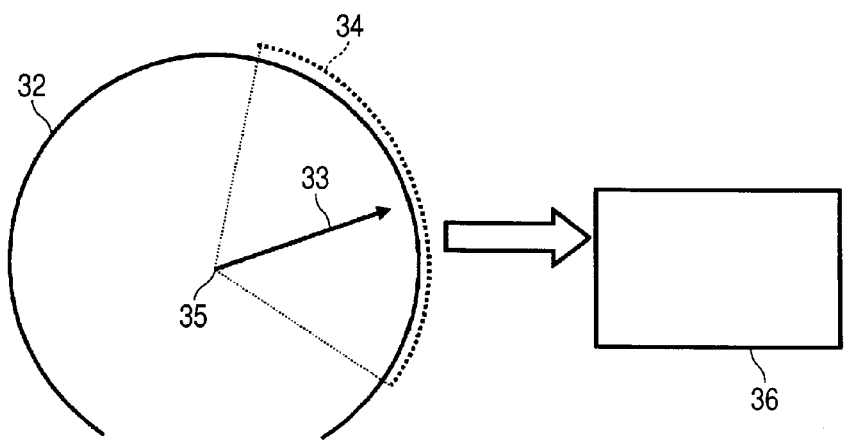

FIGS. 10, 11A and 11B are a flowchart and schematic representations for producing fly through display of an endoscope image in a preview image of the embodiment of the invention. As shown in FIG. 11A, to generate preview image data, a projection plane 30 which is wider than a display image is set, and preview image data is constructed from projected information projected from a view point 31 onto the projection plane 30 (step S61 in FIG. 10). In this case, a plurality of preview images exists according to the position of the view point on the path and therefore a plurality of preview image data is stored (step S62).

Next, to display a preview image, as shown in FIG. 11B, an image range 34 is set in a sight line direction 33 from a view point 35 and a part of a projection plane 32 is taken out for display as a display image 36 (step S63). Accordingly, it is made possible to dynamically change the sight line direction even for the preview image, and the user can find the region of interest rapidly.

In fly through display of the related endoscope image, volume rendering is performed iteratively for the view point moving on the path, whereby the user can change the sight line direction as the user desires. In fly through display of the preview image in the embodiment, a plurality of "preview image data" which is two-dimensional data on the projection plane exists in association with the position of the view point on the path, and therefore the sight line direction can be changed dynamically by performing simple processing for the preview image.

Figure 12A:
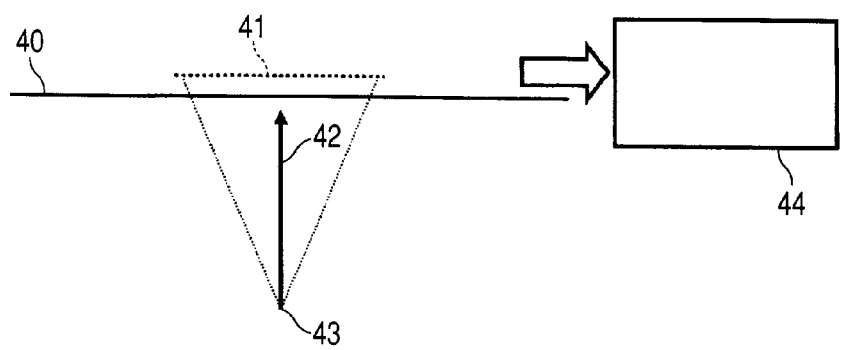
FIGS. 12A and 12B are schematic representations to show a correction method for producing fly through display of an endoscope image in one embodiment of the invention.
Figure 12B:
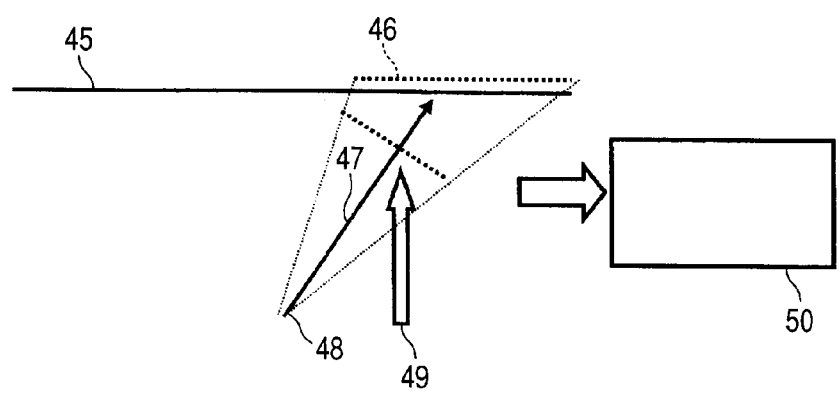
Figures 13A, 13B, 13C:
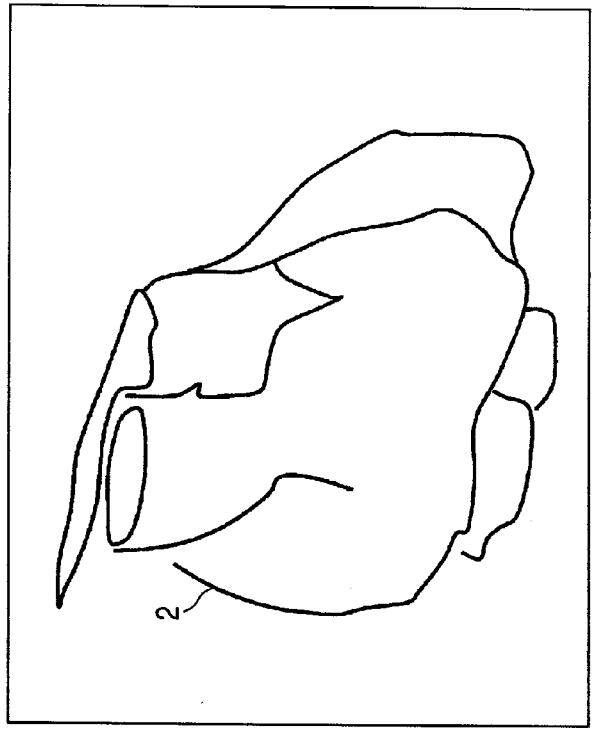
FIGS. 13A and 13B are menus to select patient and object in a related art.
FIG. 13C shows a preview image in the related art when "patient D" and "heart 2" are selected out of menus shown in FIGS. 13A and 13B.
Figure 14:
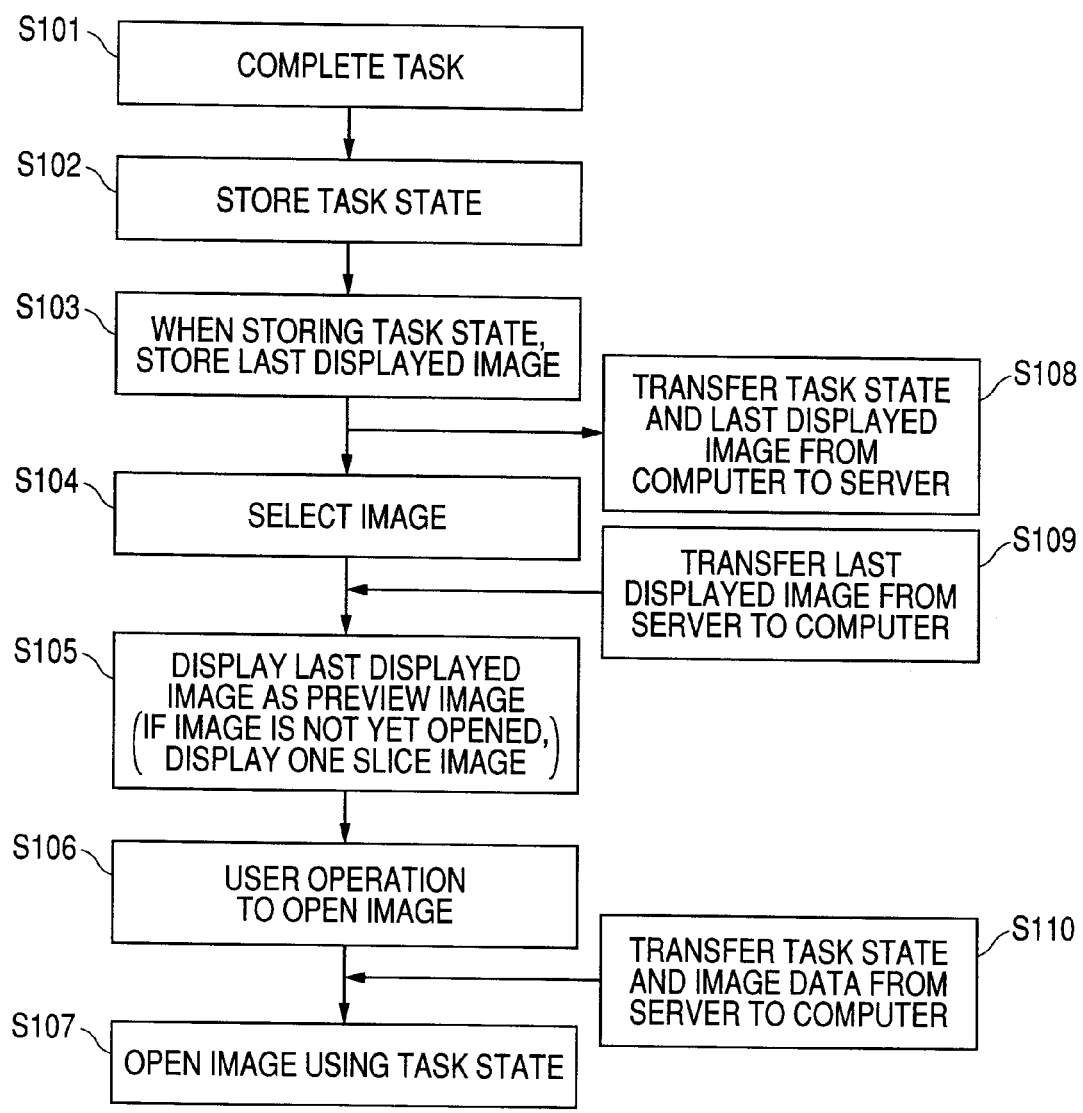
FIG. 14 is a flowchart in a related art for opening an image.
Figure 15:
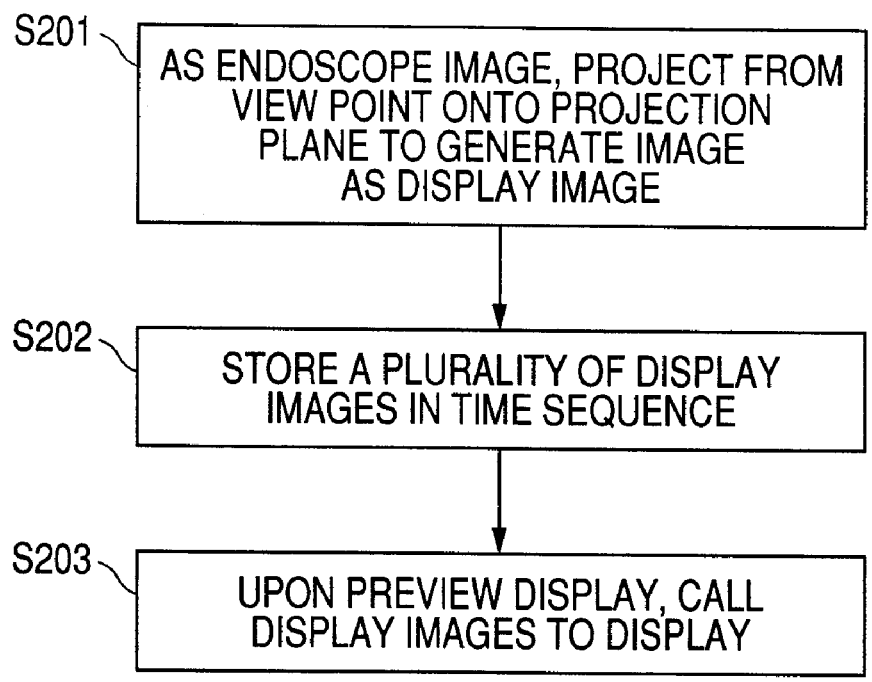
FIG. 15 shows an example of fly through display of a virtual endoscope image in the related art.
Figure 16:
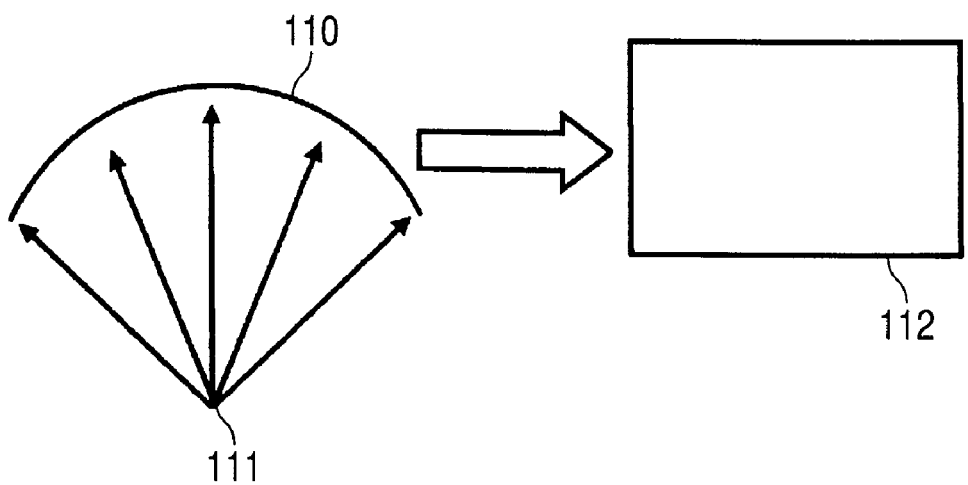
FIG. 16 is a schematic representation of the fly through display in the related art.

FIGS. 12A and 12B show a correction method when a preview image is generated by performing projection onto a plane in the embodiment of the invention. FIG. 12A shows a case where a sight line direction 42 is set at right angles to a projection plane 40 from a view point 43 and the center part of the projection plane 40 is set in an image range 41 and image display 44 is produced. On the other hand, FIG. 12B shows a case where a sight line direction 47 is set in a slanting direction from a view point 48 and a marginal part of a projection plane 45 is adopted as an image range 46.

As shown in FIG. 12B, to adopt the marginal part of the projection plane 45 as an image range 46, image display 50 is produced by assuming that an image is projected onto a correction plane 49. Thus, even if an endoscope image is projected onto a plane, pixel interpolation is conducted and distortion is corrected, whereby a clear image with less distortion can be displayed.

In the above embodiment, it is desirable that not only the preview image data and the task state, but also an image generated as a result of the previous task by the user be stored. The stored image can be displayed as a preview image. In this case, the image cannot directly be operated by the user, and thus when preview image operation from the user is accepted, a preview image is generated using preview image data and the generated preview image is displayed. In so doing, instead of the preview image generated using preview image data whose image quality may be degraded, the preview image before user operation is accepted can be a high-quality image generated by using volume data, so that the convenience provided when the user does not operate the preview image can be guaranteed.

In the embodiment, preview image data is generated with respect to volume data. However, preview image data may also be generated with respect to a combination of image data and task state, because more than one task state may be generated as a result of rendering a plurality of features involved in the same image data under different conditions. For example, the task state for enhancing an organ, the task state for enhancing the blood stream, and the task state for enhancing a bone may exist for one image data. More than one task state may also exist for one image data by applying a different filter or extraction algorithm, etc.

An embodiment of the invention can be also achieved by a computer readable medium in which a program code (an executable program, an intermediate code program, and a source program) according to the above described image processing method is stored so that a computer can read it, and by allowing the computer (or a CPU or an MCU) to read out the program (software) stored in the storage medium and to execute it.

The computer readable medium includes, for example, a tape-type medium, such as a magnetic tape or a cassette tape, a disc-type medium including a magnetic disc, such as a floppy (a registered trademark) disc or a hard disc, and an optical disc, such as CD-ROM/MO/MD/DVD/CD-R, a card-type medium, such as an IC card (including a memory card) or an optical card, and a semiconductor memory, such as a mask ROM, an EPROM, an EEPROM, or a flash ROM.

Further, the computer may be constituted such that it can be connected to a communication network, and the program may be supplied thereto through the communication network. The communication network includes, for example, the Internet, the Intranet, an intranet, an extranet, a LAN, an ISDN, a VAN, a CATV communication network, a virtual private network, telephone lines, a mobile communication network, and a satellite communication network. A transmission medium for constituting the communication network includes, for example, wire lines, such as IEEE1394, USB, power lines, cable TV lines, telephone lines, and ADSL lines, infrared rays, such as IrDA or a remote controller, and wireless lines, such as Bluetooth (a registered trademark), 802.11 Wireless, HDR, a mobile communication network, satellite lines, and a terrestrial digital broadcasting network. In addition, the program may be incorporated into carrier waves and then transmitted in the form of computer data signals.

It will be apparent to those skilled in the art that various modifications and variations can be made to the described preferred embodiments of the present invention without departing from the spirit or scope of the invention. Thus, it is intended that the present invention cover all modifications and variations of this invention consistent with the scope of the appended claims and their equivalents.

What is claimed is:

1. An image processing method comprising:
generating, by a server, a plurality of task states;
creating, by the server, preview image data from volume data and the task states;
transferring the plurality of task states to a client;
selecting, by a user, a task state;
transferring preview image data corresponding to the selected task state to the client;
generating a preview image of an original image using the preview image data corresponding to the selected task state and the selected task state;
accepting, by the client, user operation on the preview image;
transferring the volume data to the client; and
displaying the original image corresponding to and different from the preview image of the original image in response to an instruction to display the original image, wherein the operation on the preview image of the original image is reflected in the original image.

2. The image processing method as claimed in claim 1, wherein the preview image data include surface data that are prepared based on the volume data.

3. The image processing method as claimed in claim 1, wherein the preview image data include a plurality of two-dimensional images that is prepared based on the volume data.

4. The image processing method as claimed in claim 1, wherein the preview image data are automatically prepared.

5. The image processing method as claimed in claim 4, wherein the preview image data are prepared by using completion of a task by a user as a trigger.

6. The image processing method as claimed in claim 4, wherein the preview image data are prepared by using storing of the volume data as a trigger.

7. The image processing method as claimed in claim 6, wherein initial values of a task state for the preview image are generated by using acquisition of the volume data as a trigger, and
the preview image is generated by using the preview image data and the initial values of the task state.

8. The image processing method as claimed in claim 4, wherein the prepared preview image data are stored in a server.

9. The image processing method as claimed in claim 4, wherein the prepared preview image data are stored in a client.

10. The image processing method as claimed in claim 1, further comprising:
displaying an image being generated as a result of a task by a user.

11. A computer readable medium having a program including instructions for permitting a computer to perform image processing, the instructions comprising:
generating, by a server, a plurality of task states;
creating, by the server, preview image data from volume data and the task states;
transferring the plurality of task states to a client;
selecting, by a user, a task state;
transferring the preview image data corresponding to the selected task state to the client;
generating a preview image of an original image using the preview image data corresponding to the selected task state and the selected task state;
accepting, by the client, user operation on the preview image;
transferring the volume data to the client; and
displaying the original image corresponding to and different from the preview image of the original image in response to an instruction to display the original image, wherein the operation on the preview image of the original image is reflected in the original image.

* * * * *